(12) United States Patent
Winslow

(10) Patent No.: US 11,413,110 B2
(45) Date of Patent: Aug. 16, 2022

(54) HANDS FREE MEDICAL LIGHT WITH SELECTIVE INTENSITY

(71) Applicant: Jelani Winslow, Alhambra, CA (US)

(72) Inventor: Jelani Winslow, Alhambra, CA (US)

(*) Notice: Subject to any disclaimer, the term of this patent is extended or adjusted under 35 U.S.C. 154(b) by 0 days.

(21) Appl. No.: 17/470,304

(22) Filed: Sep. 9, 2021

(65) Prior Publication Data

US 2022/0104909 A1 Apr. 7, 2022

Related U.S. Application Data

(63) Continuation-in-part of application No. 16/905,017, filed on Jun. 18, 2020, now abandoned.

(51) Int. Cl.
*A61B 90/35* (2016.01)
*A61B 90/50* (2016.01)
*A61B 90/30* (2016.01)

(52) U.S. Cl.
CPC ............ *A61B 90/35* (2016.02); *A61B 90/50* (2016.02); *A61B 2090/309* (2016.02); *A61B 2090/502* (2016.02); *A61B 2562/0271* (2013.01)

(58) Field of Classification Search
CPC ................ A61B 2090/502; A61B 1/0692
See application file for complete search history.

(56) References Cited

U.S. PATENT DOCUMENTS

| 7,008,074 | B1 |  | 3/2006 | Halm |  |
| 8,550,664 | B1 | * | 10/2013 | Nguyen | G02B 7/006 362/323 |
| RE46,463 | E |  | 7/2017 | Fienbloom et al. |  |
| 9,968,417 | B2 |  | 5/2018 | Johnson et al. |  |
| 2008/0106906 | A1 | * | 5/2008 | Lewsadder | F21V 9/08 362/322 |
| 2011/0227509 | A1 |  | 9/2011 | Saleh |  |
| 2015/0305111 | A1 | * | 10/2015 | Bortolotti | F21V 21/084 362/105 |
| 2017/0007351 | A1 | * | 1/2017 | Yu | G02B 27/0172 |
| 2017/0202633 | A1 | * | 7/2017 | Liu | A61B 90/37 |
| 2018/0224674 | A1 | * | 8/2018 | Carabin | G02C 11/10 |

FOREIGN PATENT DOCUMENTS

CN 107005006 A * 8/2017 ........... B64C 39/024

OTHER PUBLICATIONS

English translation of CN-107005006-A Wu, published Aug. 2017 (Year: 2017).*

* cited by examiner

*Primary Examiner* — Evan P Dzierzynski

(74) *Attorney, Agent, or Firm* — Harpman & Harpman

(57) ABSTRACT

A hands free integrated personal task lighting system for dental or surgical use providing remote control light activation and selective adjustable light intensity output. A fixed output value light source on a headset has an electronically activated variable transmission glass which changes transparency to degrees of translucentness by varied electrical activation. The light system provides both remote light activation and illumination value control by variable control sensors in a hands-free environment including temperature sensing activation control.

1 Claim, 7 Drawing Sheets

HANDS FREE MEDICAL LIGHT WITH SELECTIVE INTENSITY

This application is a Continuation in Part of Ser. No. 16/905,017, filed Jun. 18, 2020.

BACKGROUND OF THE INVENTION

1. Technical Field

This invention relates to dental and surgical procedure lights, specifically hands-free task lighting on headsets controlled for proper light intensity.

It is understood that proper strong directed light is required for illumination of treatment areas in medical procedures or in dentistry where the patient's mouth must be illuminated to assist in the procedure required. It is also known that the intensity of such light needs to be varied for certain dental practice requirements. Medical/dental head lamp lighting systems provide a solution by directing illumination directly to the viewing area in a hands-free configuration, as needed.

2. Description of Prior Art

Prior art medical/dental head lamps provide for hands free task lighting source with on and off activation by switching from a remote power source thereto. Examples of such head light task lighting systems can be seen in U.S. Pat. Nos. 7,008,074, 9,968,417, re-issued patent RE46463E and U.S. Publication 2011/0227059.

In U.S. Pat. No. 7,008,074, a hands-free control light is disclosed having a controllable light source on a pair of glasses. A light controlled by switches positioned at different angles so the operator moves their head to point at the first infrared center switch and remotely located infrared source, the first infrared switch will activate the dim light similarity the operator moves their head to point the second infrared sensor switch at the infrared source, the light will be turned on and off.

U.S. Pat. No. 9,968,417 discloses a hands-free lighting system having a master control unit, a light unit and a remote-control unit. The operator can control the head mounted light remotely through the control system.

In re-issued patent RE46463, a remote-controlled illumination head lamp attached to a headset on a headband of the user is shown. Sensing unit within the control provides for on/off activation by detection of motion in front of the sensing unit. Illumination is increased and decreased based on power control supplied to the lamp.

SUMMARY OF THE INVENTION

A touch free, hands-free lighting system for dental or surgical use having a primary light source with a variable transparent optical lens capable of user control variation of light transmission induced by response to applied voltage defined generally as switchable glass. Control activation and degree initiation by varied sensor activation means such as motion, ambient light levels, sound and voice detection, proximity detection and/or RFID driven control sensor systems.

DETAILED DESCRIPTION OF THE INVENTION

Figure 1:
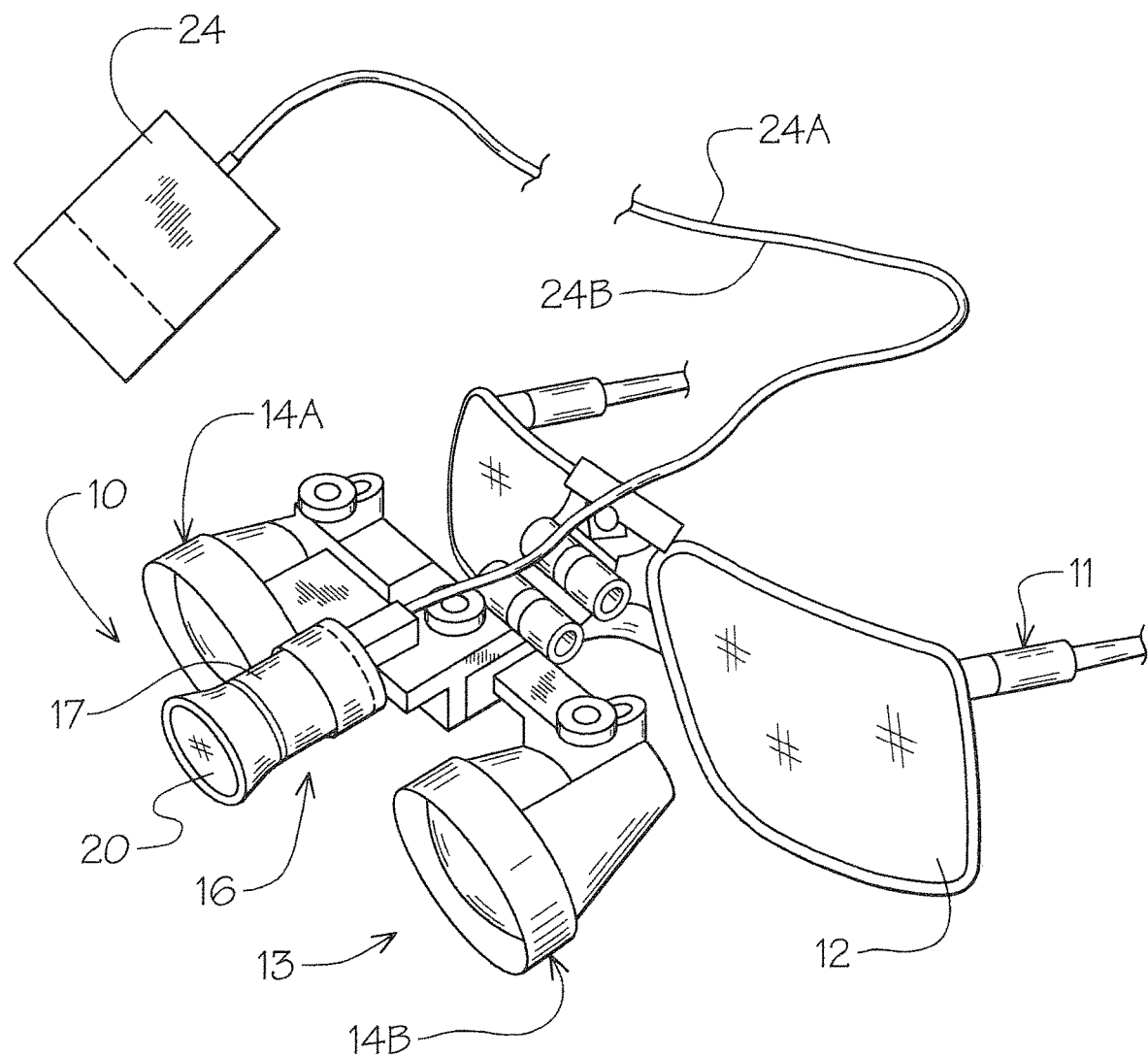
FIG. 1 is a perspective graphic view of the lighting system of the invention on a headlight and magnification glasses assembly.

Referring to FIG. 1 of the drawings, in the example, magnifying glasses 10 can be seen with a central illuminated source light having an eyeglass support frame 11 with a pair of transparent lenses 12. A dual optical magnifying lens assembly 13 is attached centrally to the eyeglass frame 11 having a pair of spaced magnifying optics 14A and 14B on a bifurcated mounting bracket 15.

Figure 2:
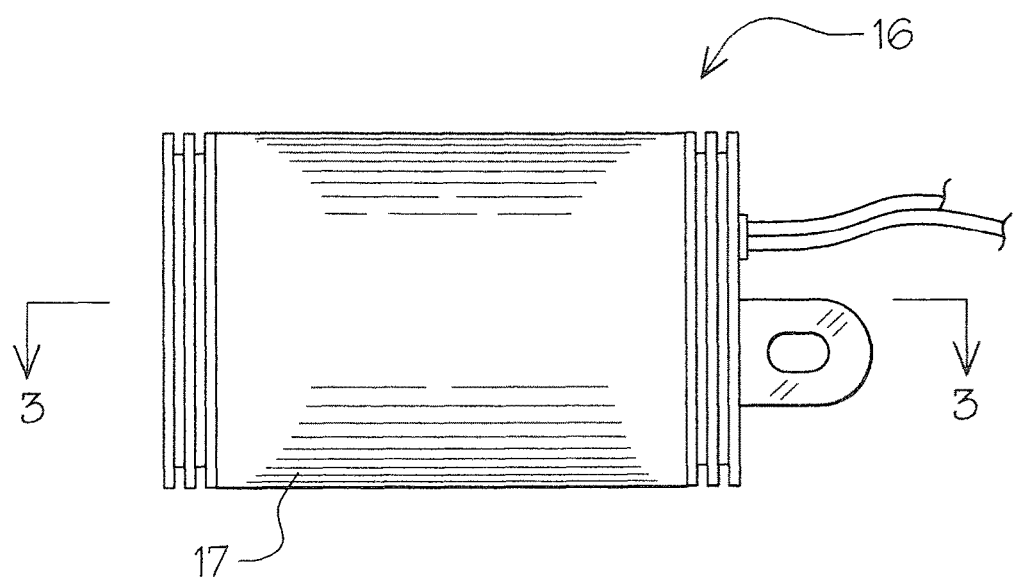
FIG. 2 is an enlarged side elevational view of the lighting assembly of the invention with adjustable optical switchable glass.
Figure 3:
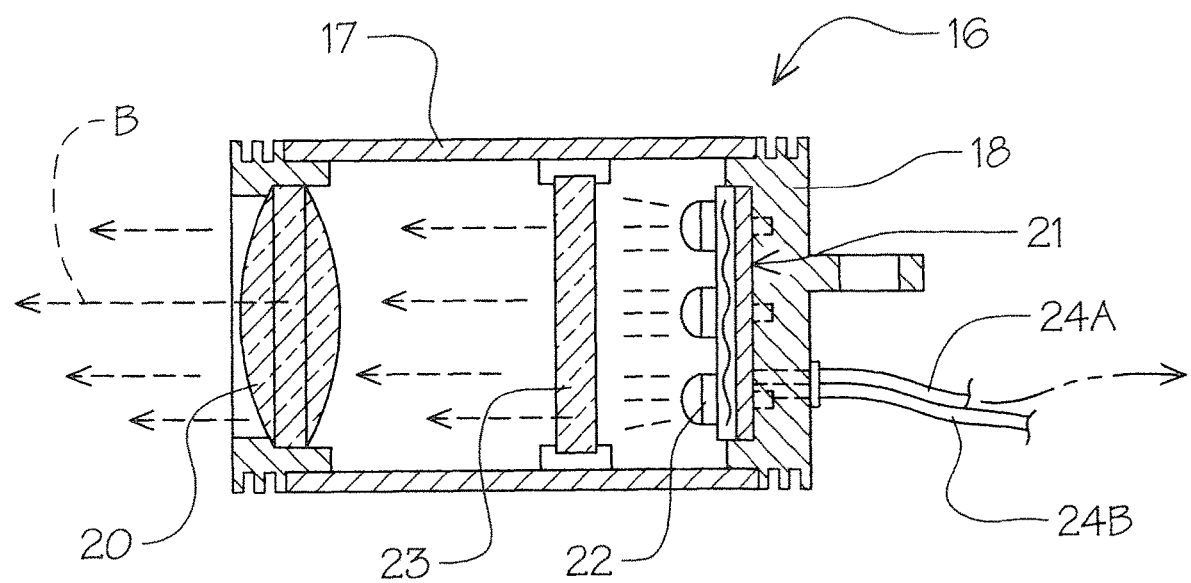
FIG. 3 is an enlarged cross-sectional view on lines 3-3 of FIG. 2 in non-activated form.
Figure 4:
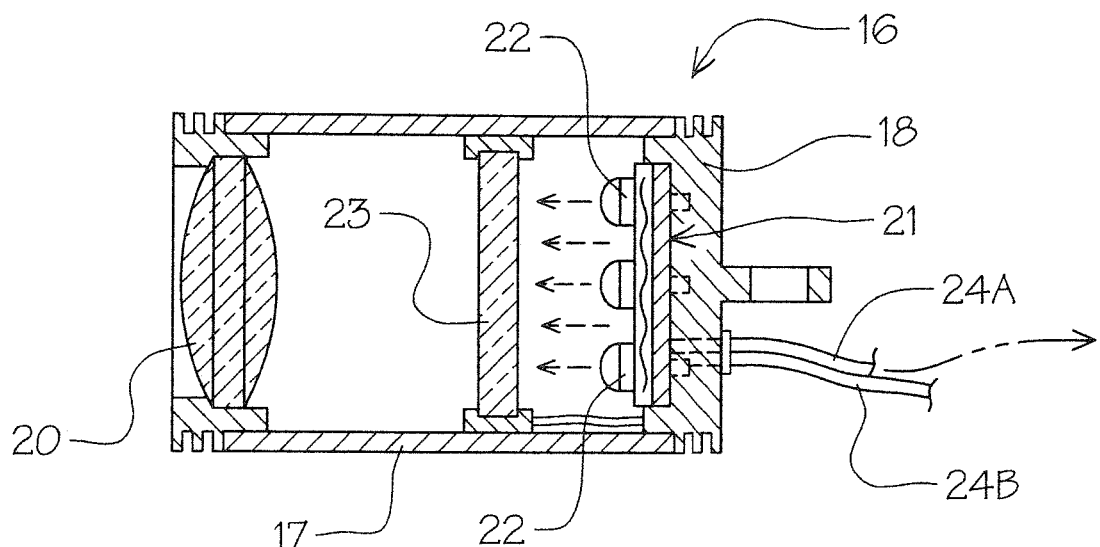
FIG. 4 is an enlarged cross-sectional view on lines 3-3 of FIG. 2 in activated light output form.

The centralized illumination source is achieved by a controllable light output lighting assembly 16 positioned centrally on the frame between the respective frame lens 12 and extending outwardly therefrom. The variable lighting assembly 16 as best seen in FIGS. 2-4 of the drawings has a cylindrical housing 17 with an annular closed base end 18 and an oppositely disposed open apertured lens mount 19. A transparent focusing lens 20 is secured within the lens mount 19 opening determining the effective projective light field therefrom. A light source defined in this example as a multiple LED light assembly 21 having a high intensity LED's 22 mounting on a support circuit board 23 is secured to the inner surface 18A of the closed base end 18 which has control and power supply access wiring openings 18B therein.

The LED lighting assembly 21 is in longitudinal alignment with the focusing lens 20 for projecting a task lighting beam B therefrom.

A remote power supply and control module 24, as best seen in FIG. 1 of the drawings, provides power and activation controller for both the LED lighting assembly 21 and a smart glass panel 23, via respective power links 24A and 24B.

Referring now to FIGS. 3 and 4 of the drawings, the smart glass i.e. switchable glass panel 23 is mounted within the cylindrical housing 17 in longitudinally spaced relation to both the LED light assembly 21 and the transparent focusing lens 20. The switchable glass panel 23 is in electrical communication, as noted, with the power control module 24 by the respective power links 24A and 24B extending from the cylindrical housing 17. The switchable glass panel 23 is known within the art as having the ability to change its light transmission properties from transparent to opaque in response to applied voltage variations. This provides the ability to vary the light beam field transmission there through from the hereinbefore described LED light assembly 21 during operation at a constant light output.

Such switchable glass panels 23, for example, suspended particle devices SPD or polymer-dispersed liquid-crystal devices PDLCs can be used. SPD device which uses a thin film of laminate of rod-like nano-scaled particles is suspended in a liquid and placed between two pieces of glass or plastic or attached to one layer. When no voltage is applied, the suspended particles are randomly organized, thus blocking the absorbing light. When voltage is applied, the suspended particles align and let light pass. Varying the voltage of the film varies the orientation of the suspended particles thereby regulating the effective opaqueness of the glazing and the amount of light transmission.

Independent initiation of control voltage may be by any number of various activation sensors, not shown, output to the power and control module 24 which are inclusive of but not limited to motion, ambient light, sound such as voice commands and/or RFID light sensor configurations which are commercially available and well known within the art.

It will be evident from the above description that the effective lighting intensity output thereby is controlled solely by the switchable glass panel 23 so that the high intensity LED's 22 may remain constant in their effective light output during use.

As noted, the power and control module 24 can provide preprogrammed voltage control levels in response to sensor activation. A rechargeable battery drives the power and control module 24, thus providing portability to the light assembly system, in general. It will also be evident that in view of the above description that a variety of lighting assemblies 16 mounting configurations may also be used with or without the applied magnifying glass 14A and 14B used for illustration, in this example.

Figure 5:
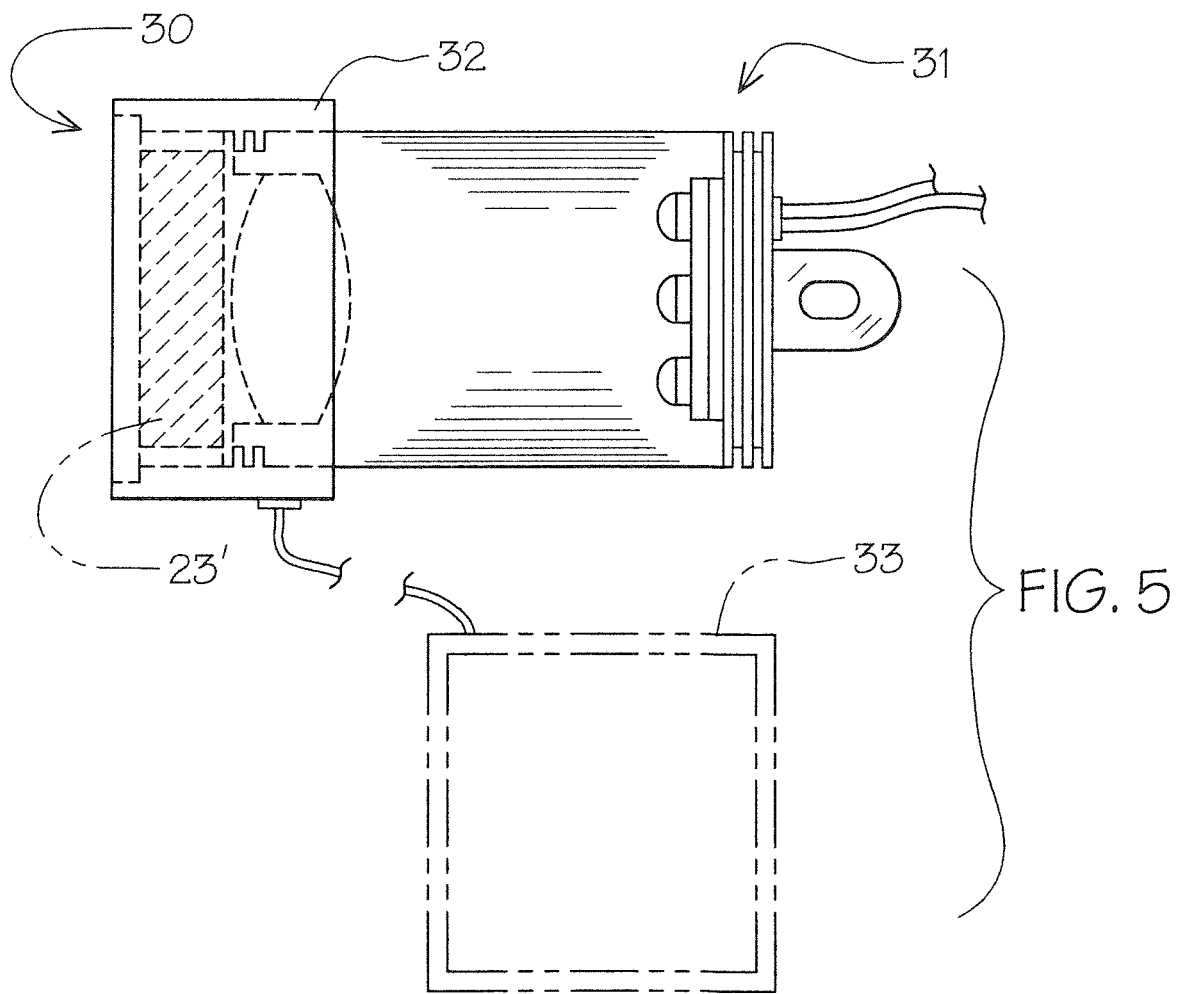
FIG. 5 is an enlarged side elevational view of an alternate lighting assembly for attachment to existing headlight source devices.

Referring now to FIG. 5 of the drawings, an adaptable switch glass assembly attachment 30 can be seen secured on a hands-free head light source assembly 31 representative of those available within the industry. The switch glass assembly attachment 30 has an adaptable mounting housing 32 that will be attached externally to existing headlight assemblies 31 to provide an externally mounted switchable glass panel 23' application having the same adaptable and changeable optical qualities as hereinbefore described in the primary form of the invention's switchable glass panel 23. As before a remote power and control module 33 is needed and is shown graphically for illustration purposes in broken lines only to meet the requirement of an enabling disclosure.

Figure 6:
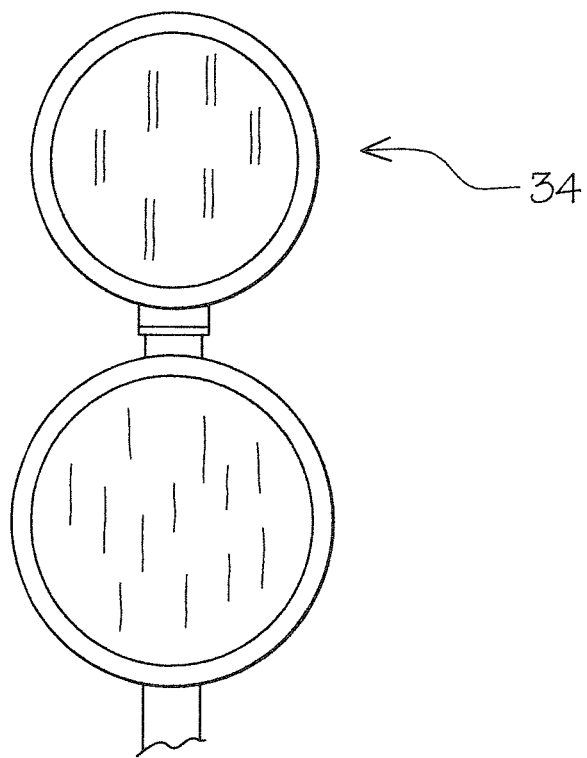
FIG. 6 is a partial, front elevational view of a flip down dental light filter assembly in open position.
Figure 7:
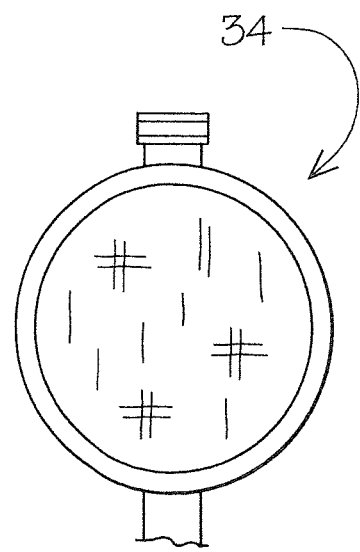
FIG. 7 is a partial front elevational view of a flip down dental light filter assembly in closed used position.

Referring now to FIGS. 6 and 7 of the drawings, other task specific attachments may be used with the hereinbefore described system of the invention such as a standard headlight flip filter 34 of a traditional orange filter medium applicable to dental filters which is flipped down to block blue light from passing from the light assembly as required during dental filling light activated material hardening parameters as an example of same.

Figure 8:
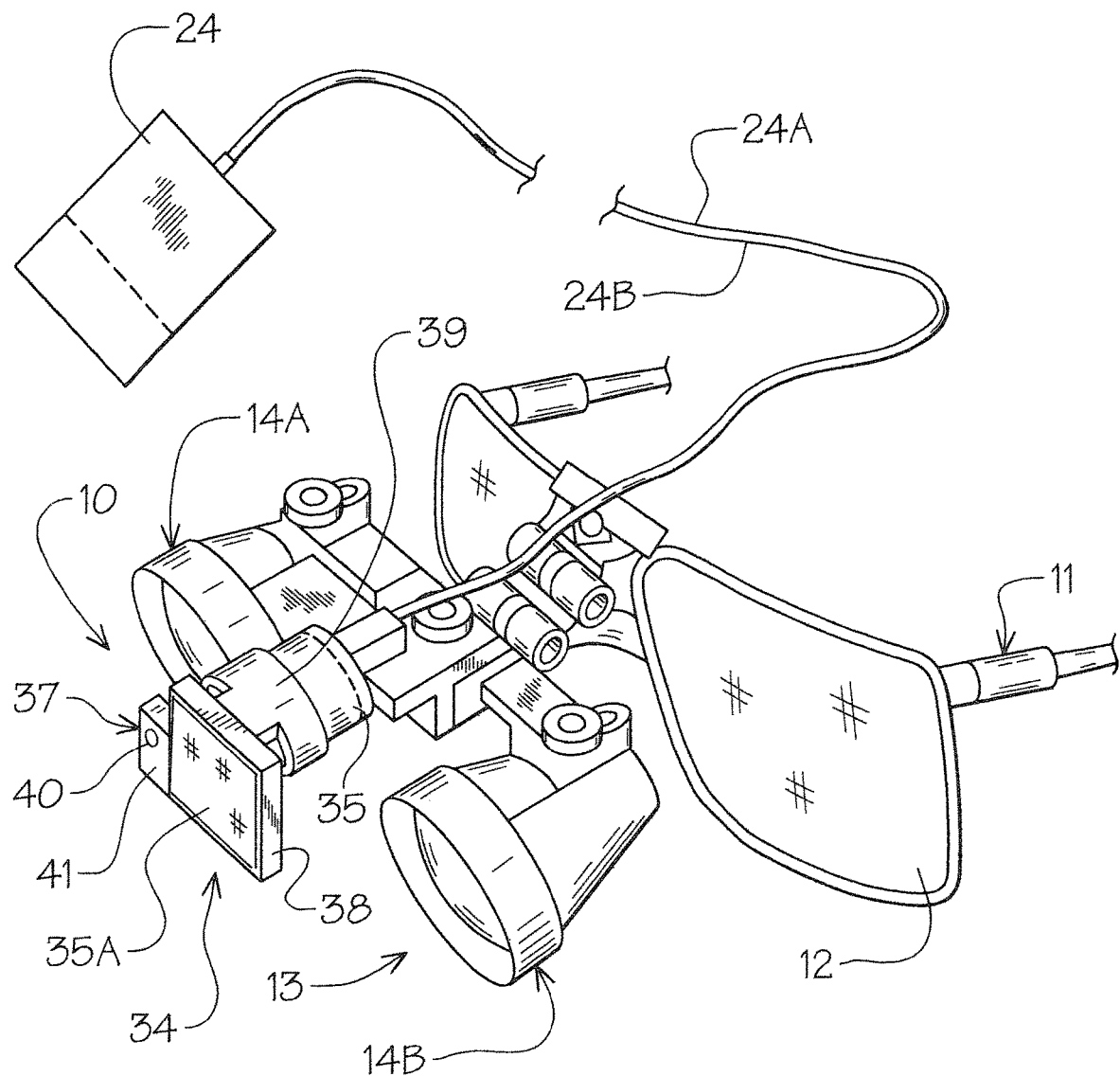
FIG. 8 is a perspective graphic view of an alternate light control system with temperature warning.
Figure 9:
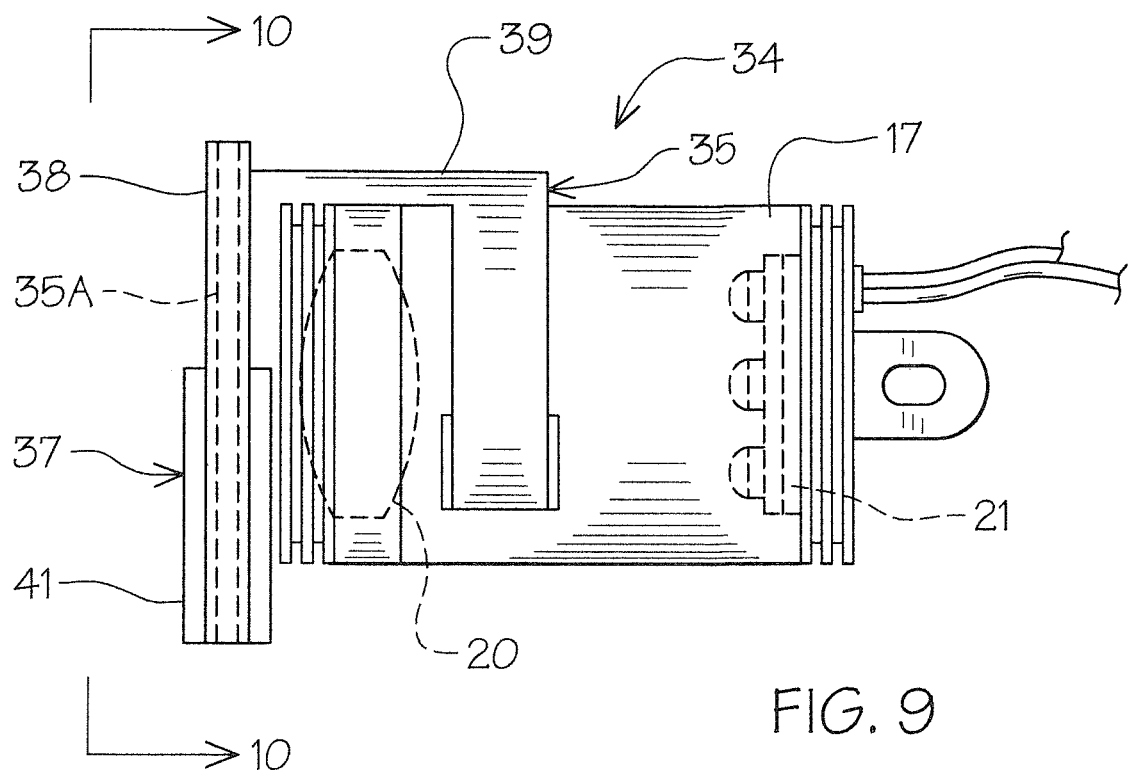
FIG. 9 is an enlarged side elevational view of the alternate light control system.
Figure 10:
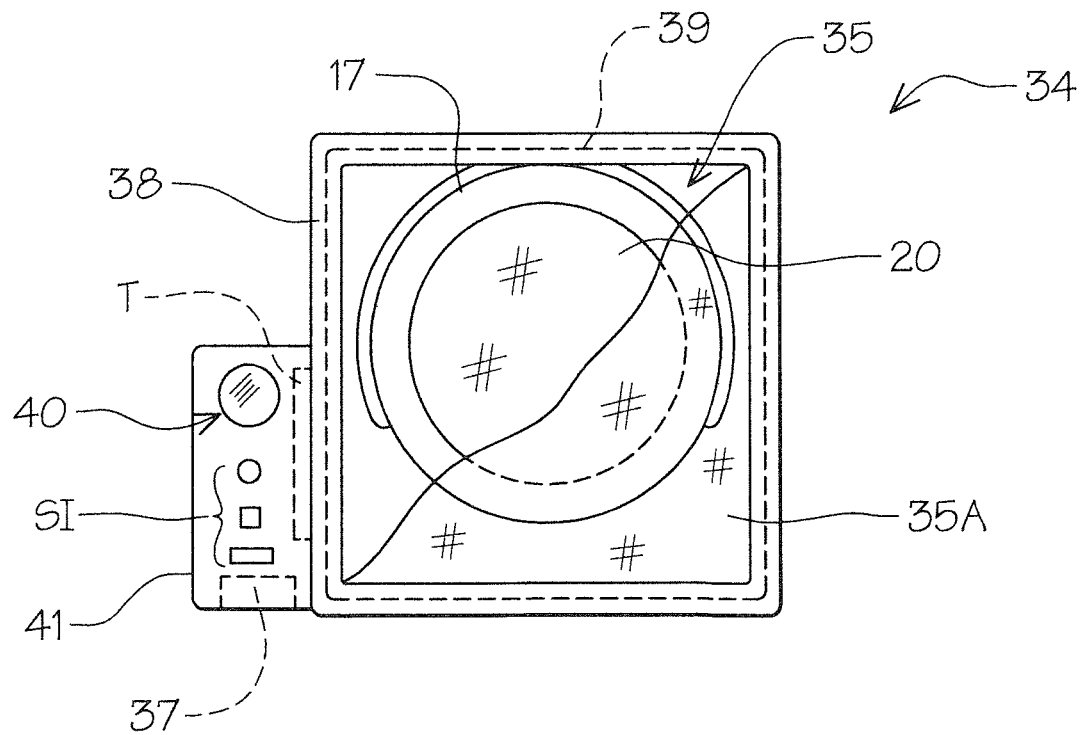
FIG. 10 is an enlarged front elevational view on lines 10-10 of FIG. 9.

Referring now to FIGS. 8-10 of the drawings, an alternate form of the touch free, hands free adapted lighting system 34 of the invention can be seen having an auxiliary control mounting lens housing 35 for attachment to an existing hands-free task light, not shown, or as illustrated on the magnifying glass 10 as hereinbefore described in the primary form. The adaptable light filter system 34 has a transparent focusing lens 20 shown in both broken and solid lines in FIGS. 9 and 10 of the drawings respectively shown within the cylinder housing 17 with an integral light generating source 21 and remote control and power supply modules 24, again as hereinbefore described in the primary form of the disclosed invention.

The adaptable lighting filter system 34 has an independent exterior switchable glass panel 35A in electrical communication with an independent battery power supply 37 supported with a frame housing 38 extending from and selectively secured to a contoured support mount 39 to the cylinder housing 17 in this example.

The adaptable lighting filter and control system 34 will provide selectively controlled observable light intensity by electronically controlling the relative transparency of the switchable glass panel 35A acting as a "shutter glass" in this application. The control is achieved by an independent hands-free sensor assembly 40 integral with a control and power source secondary housing 41. Such control sensor of the adaptable lighting system 34 may include, but not be limited to sensor input such as relative motion, ambient light levels, sound and voice direction proximity as well as wireless control via RFID in which all such input sensory controls are well known and established within the art and are adaptable to the present control system.

A temperature warning application allows for monitoring of the "fixture" temperature and it is preprogrammed through a logic control circuit C to react to a predetermined temperature threshold causing the light output to strobe by activation of the switchable glass panel 35A with a preprogrammed voltage level activating the optical properties of the switch glass panel 37 in an on and off configuration indicating a warning strobe effect to alert the user, not shown, that the light fixture is too hot to touch.

Figure 11:
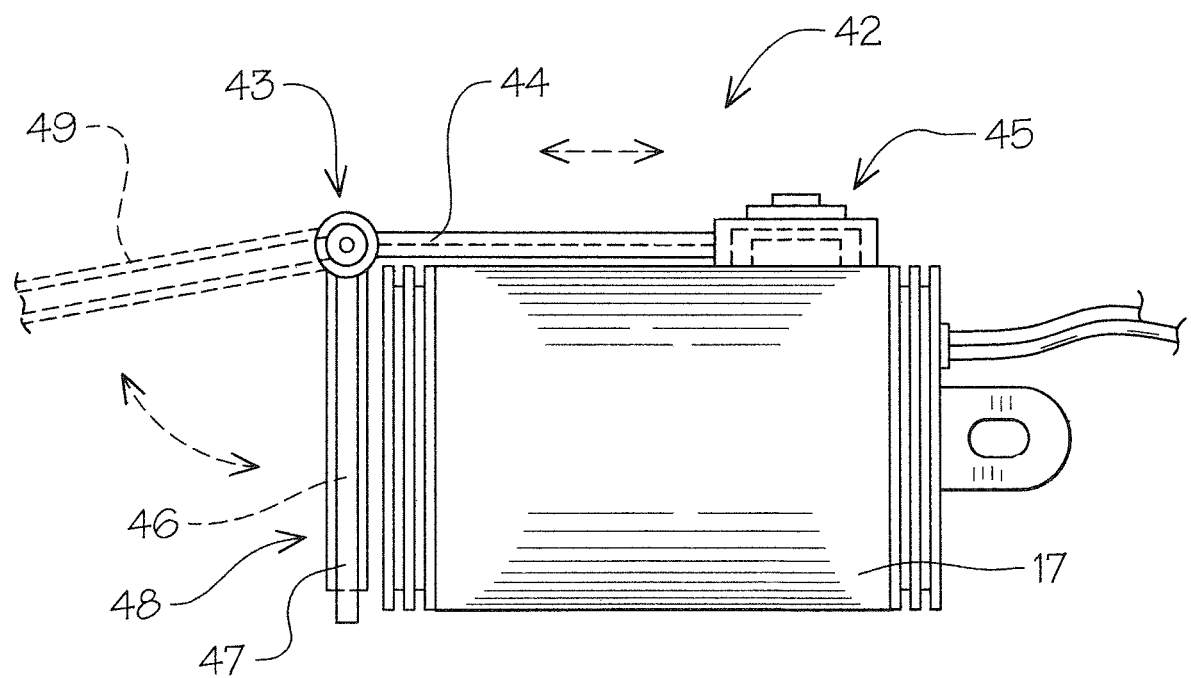
FIG. 11 is an enlarged side elevational view of a second alternate light control system with deployable color filter.

A secondary feature of the adaptable light filter system 42 is the use of a retractable color filter assembly 43 using a mechanical activated filter support frame and interconnected linkage 44 with a sensor power assembly 45 as illustrated in FIG. 11 of the drawings.

A color filter lens 46 within a support frame 47 will pivot from a light path engagement position at 48 to a secondary non-engagement position at 49 shown in broken lines.

An independent sensor power assembly provides activation to armature linkage via linear activator. A temperature sensor determines the light fixture's temperature to institute a preprogrammed warning sequence, as noted, which can be either independently or in combination with the hereinbefore described auxiliary control mounted lens 35.

Thus, it will be seen that a new and useful hands free medical/dental headlight lighting intensity system has been illustrated and described in both internal and external application configurations which will provide a unique and novel hands-free task lighting source which intensity is controllable through the application of switchable glass 23 and 23' which transmission qualities can be varied by pre-selected voltage inputs thereto as hereinbefore described.

Such light intensity systems have been illustrated and described herewith and it will be seen that various changes and modifications may be made thereto without departing from the spirit of the invention.

Therefore, I claim:

1. A hands free variable task lighting system for medical procedures comprises,
   a primary control module, a light assembly, a source of power,
   said primary control module configured for illumination control of said light assembly by selective power supply voltage to said assembly,
   said lighting assembly comprising,
   a light source having at least one high intensity LED in communication with said source of power, a selectively activated smart glass panel optically transparency responsive to varied voltage from said control module upon receiving a signal from a control input device, said smart glass panel within a frame housing extending from a contoured support mount on said light assembly in optical alignment with said light source, at least one user control receiving input from a user, said user control comprising at least one of said control input devices, an independent light fixture temperature sensor and control logic circuit in communication with said temperature sensor and said smart glass panel preprogrammed to threshold activation by light source temperature for sequential warning light output control of smart glass.

* * * * *